(12) United States Patent
Rasmussen et al.

(10) Patent No.: US 7,780,642 B2
(45) Date of Patent: Aug. 24, 2010

(54) SHEATH ADHESIVE IN BANDS

(75) Inventors: Anders Bo Rasmussen, Vanloese (DK); Henrik Bork Bjerregaard, Bronshoej (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 11/661,257

(22) PCT Filed: Aug. 29, 2005

(86) PCT No.: PCT/DK2005/000549

§ 371 (c)(1),
(2), (4) Date: Feb. 4, 2008

(87) PCT Pub. No.: WO2006/021220

PCT Pub. Date: Mar. 2, 2006

(65) Prior Publication Data

US 2008/0249489 A1    Oct. 9, 2008

(30) Foreign Application Priority Data

Aug. 27, 2004   (DK) ............................. 2004 01292

(51) Int. Cl.
*A61F 5/44* (2006.01)
*A61M 1/00* (2006.01)
*A61M 27/00* (2006.01)

(52) U.S. Cl. .................. 604/352; 604/540; 604/544; 604/541; 604/349

(58) Field of Classification Search ................ 604/352, 604/541, 544, 349
See application file for complete search history.

(56) References Cited

U.S. PATENT DOCUMENTS

| | | | | | |
|---|---|---|---|---|---|
| 4,378,018 | A | * | 3/1983 | Alexander et al. | 604/350 |
| 4,427,737 | A | * | 1/1984 | Cilento et al. | 428/315.7 |
| 4,775,374 | A | * | 10/1988 | Cilento et al. | 604/344 |
| 4,846,909 | A | | 7/1989 | Klug et al. | |
| 4,865,595 | A | * | 9/1989 | Heyden | 604/352 |
| 4,885,049 | A | | 12/1989 | Johannesson | |
| 5,059,189 | A | * | 10/1991 | Cilento et al. | 604/307 |
| 5,270,358 | A | * | 12/1993 | Asmus | 524/55 |
| 5,714,225 | A | * | 2/1998 | Hansen et al. | 428/114 |
| 6,326,421 | B1 | * | 12/2001 | Lipman | 524/22 |
| 6,355,022 | B1 | * | 3/2002 | Osborn et al. | 604/385.17 |
| 6,372,951 | B1 | * | 4/2002 | Ter-Ovanesyan et al. | 604/361 |
| 6,569,134 | B1 | * | 5/2003 | Leise et al. | 604/332 |
| 6,685,683 | B1 | * | 2/2004 | Clok et al. | 604/344 |
| 6,699,226 | B2 | * | 3/2004 | Velazquez | 604/349 |
| 6,805,690 | B2 | * | 10/2004 | Ogden et al. | 604/352 |
| 7,160,277 | B2 | * | 1/2007 | Elson et al. | 604/352 |
| 7,442,438 | B2 | * | 10/2008 | Boulos et al. | 428/355 AC |
| 2003/0073965 | A1 | * | 4/2003 | Leise et al. | 604/336 |
| 2007/0117880 | A1 | * | 5/2007 | Elson et al. | 523/118 |

FOREIGN PATENT DOCUMENTS

JP       64-22251     1/1989

* cited by examiner

*Primary Examiner*—Tatyana Zalukaeva
*Assistant Examiner*—Susan Su
(74) *Attorney, Agent, or Firm*—Coloplast Corp.; Daniel G. Chapik; Nicholas R. Baumann

(57) ABSTRACT

The present invention relates to an external urinary catheter. The present application realizes, that by replacing the traditional broad band of adhesive material with at least two bands, several advantages are obtained. As will be understood in the following, the tendency to leak is decreased, the degree of skin irritation on the penis is decreased and the adhesive characteristic can be improved.

4 Claims, 1 Drawing Sheet

SHEATH ADHESIVE IN BANDS

This is a national stage of PCT/DK05/000549 filed Aug. 29, 2005 and published in English.

FIELD OF THE INVENTION

The present invention relates to an external urinary catheter. The technology behind the invention is in the field of adhesive tack (strength).

BACKGROUND

External urinary catheters, also known as urisheaths, are conventionally used in urinary catheter devices for aiding male urinary incontinence and for use in hospitals in connection with treatment or surgery of urethral disorders. Such an external urinary catheter normally comprises a sheath or body portion enclosing the shaft of the penis, and a tip portion that is provided with a comparatively short discharge tube, which via a hose is connected to a urine collection bag that is e.g. fastened to the bed or the leg of the user.

Today, sheaths commercially known one-piece sheaths have one single band of adhesive, typically having a width of 35-45 mm. Some drawbacks of these commercially known sheaths are that leaks occurs through a single leak path developing through the wide band of adhesive. In addition, when removing a sheath, the residual tack of the adhesive will stress the skin when peeled off. Skin irritation is a known consequence of this. In worst cases, after repeated removals, the skin condition may be such, that sheaths cannot be worn until the skin has healed.

U.S. Pat. No. 4,846,909 discloses a urisheath utilizing varying patterns of pressure sensitive adhesive applied to the urisheath. Examples of such patterns include a solid band of adhesive material not greater than two inches wide, a matrix of dots of the adhesive material may be used so as to create a random dispersion of adhesive points or three bands of the adhesive material which would lessen the likelihood of skin irritation due to repeated usage of the device.

SUMMARY

The present application realizes, that by replacing the traditional broad band of adhesive material with at least two bands, several advantages are obtained. As will be understood in the following, the tendency to leak is decreased, the degree of skin irritation on the penis is decreased and the adhesive characteristic can be improved—all significant breakthroughs for the user of external urinary catheters.

The solution of this invention solves the two problems above. The solution is to split the traditional wide band of adhesive into 2 or more bands. By introducing bands, a developing leak path is broken thus delaying its progression.

Thus, the present invention provides an external urinary catheter comprising a tip portion and a sheath portion with an adhesive material on the inside of the sheath, wherein the adhesive material is located as at least two rings of adhesive material. Typically the rings are arranged perpendicular to the longitudinal axis of the sheath.

It is essential, that the rings are continuous. Preferably arranged in a circle perpendicular to the longitudinal axis of the sheath. Thereby, the first ring, counted from the tip of the external urinary catheter, will prevent urine from passing from the tip down the sheath. However, should this first ring leak, the second ring will prevent urine from passing from the tip down the sheath.

Thus, in one embodiment, the sheath comprises 2 rings of adhesive material. In an alternative embodiment, the sheath comprises 3, 4, 5, 6, 7, 8, 9 or even 10 rings of adhesive material.

In one embodiment the at least two rings of adhesive material are separated by an area.

Thereby, a second advantage of the ring system is, that in use, the sheath will not be placed in the exact same position when changing. With the adhesive in bands the same patch of skin is not repeatedly stressed thus reducing irritation of the skin. This advantage is further emphasized when the area between any two rings of adhesive material comprises a skin caring material.

In an additional or alternative embodiment, the area between any two rings of adhesive material comprises foam or similar absorbent material.

A wide range of adhesive materials exists. Such adhesives could for example be acrylics, thermoplastic hydrocollids or gel-like adhesives.

The applicant has observed a wide divergence in the effectiveness of adhesives inbetween individuals. That is, whereas one adhesive material is very well suited for some individuals, they have no, or very low adhesive properties on others. This is caused by wide changes in skin conditions inbetween individuals partly based on race, diet, lifestyle and hygiene level, but also individual, genetic properties. To obtain a urisheath that suits a range of individuals, under different conditions, one embodiment relates to an external urinary catheter as described, wherein at least one ring of adhesive material is formed of a different adhesive material than at least one other ring of adhesive material.

The at least two rings can be separated by an area, which for example can be coated with a material having properties different from the adhesive such as a skin caring material, absorber or a fluid indicator.

The at least two rings can alternatively about or overlap.

By providing an overlap advantage can be taken of the combined properties of the rings of adhesive materials.

In one embodiment alternating bands of two of more adhesive with different properties such as tack are used. In this way an unbroken length of adhesive is maintained, but with alternating properties.

In one alternative embodiment the two rings of different adhesive are applied on the inside of the urisheath in a spiralling pattern. This embodiment is relative simple to realise as it only requires two nozzles spraying adhesive while rotating and while beings displaced longitudinal relative to the urisheath.

FIGURES

DETAILED DISCLOSURE

Figure 1:
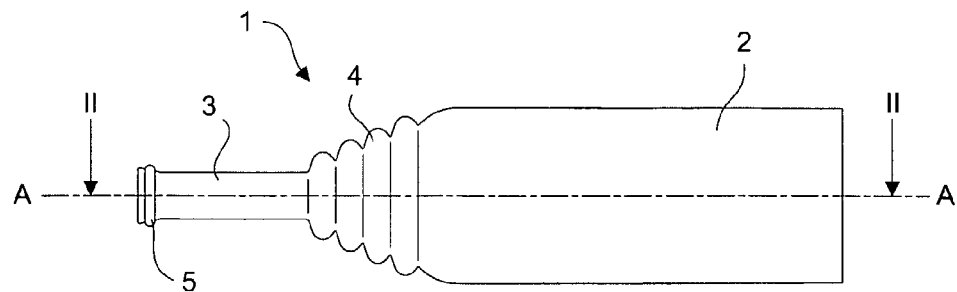
FIG. 1 shows an urisheath as provided within the art.

FIG. 1 shows an urisheath 1 as provided in the art. The urisheath have a sheath portion 2 and a tip portion 3. During use the sheath portion is applied around a penis and the tip portion is connected to a catheter.

Connecting the sheath portion 2 and the tip portion 3 there is provided a corrugated portion 4. The corrugated portion provides kink resistant means.

At the end of the tip portion there is provided a rib 5. The rib provided for improved attachment of the catheter to the tip portion.

During use the sheath portion is applied around the shaft of the penis (not shown). Typically the sheath portion is rolled onto the penis, but other means to apply the sheath portion are known within the art. However, these application methods are not relevant to the present invention and will therefore not be described further.

When the sheath portion is applied a catheter (not shown) is connected to the tip portion. The catheter is connected to a bag (not shown). This allows urine to be conducted from the penis to the bag.

Figure 2A:
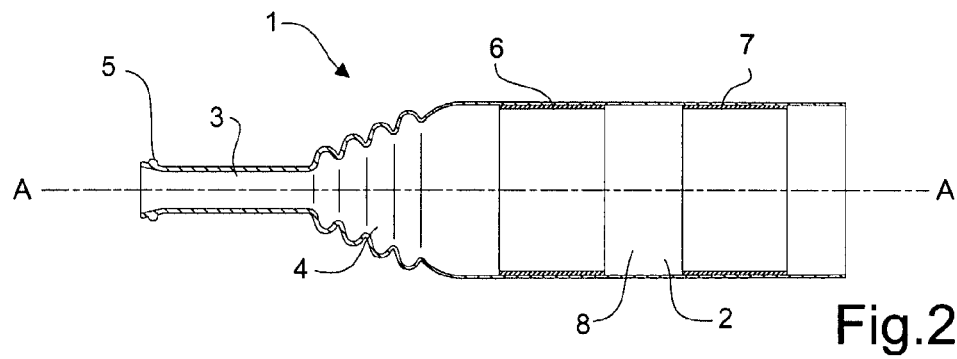
FIG. 2a-2c shows seen in section along line II-II in FIG. 1 different embodiments of the invention.

FIG. 2a shows a first embodiment of the invention. Rings of adhesive material are formed as a first adhesive band 6 and a second adhesive band 7 applied on the inside of the urisheath 1. An area 8 with no adhesive separates the two bands in the axial direction along axis A-A.

If the first adhesive band is broken there is a risk that liquid, typically urine, will leak through. It has shown that the breakage of the adhesive bands is an important factor for the sealing characteristics of the urisheath. A urisheath can be worn for days, however, due to hygienic reasons they are usually only worn for 24 hours at a time, without leaking, but when first liquid starts seeping into an adhesive band it is only a matter of hours, or less, before the seal provided by that band is broken. Thus by providing multiple adhesive bands separated by areas with no adhesives the number of barriers is proportionally increased.

Figure 2B:
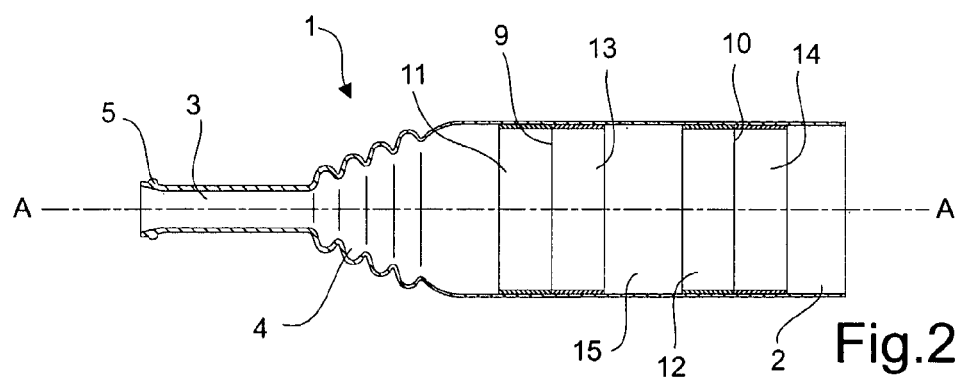

FIG. 2b shows a second embodiment of the invention. Here there are provided a first section 9 and a second section 10 of adhesive bands. Each section comprises a first adhesive band 11,12 and a second adhesive band 13,14 which abuts against each other. An area 15 with no adhesive separates the sections.

Experience shows that different skin types adhere differently to adhesives. Thus, the first and second adhesive bands are formed of different types of adhesive. Thereby an urisheath can be provided which have a broader user range.

In one example a wet-tack adhesive is be applied next to an acrylic adhesive. The wet-tack would be advantageous since it would absorb moisture while still adhering which often would be relevant since the skin typically is moist after the user has been washed. As the skin dries the acrylic adhesive will adhere.

Furthermore, by providing sections consisting of different bands of adhesives multiple leakage barriers can be provided as described above.

Figure 2C:
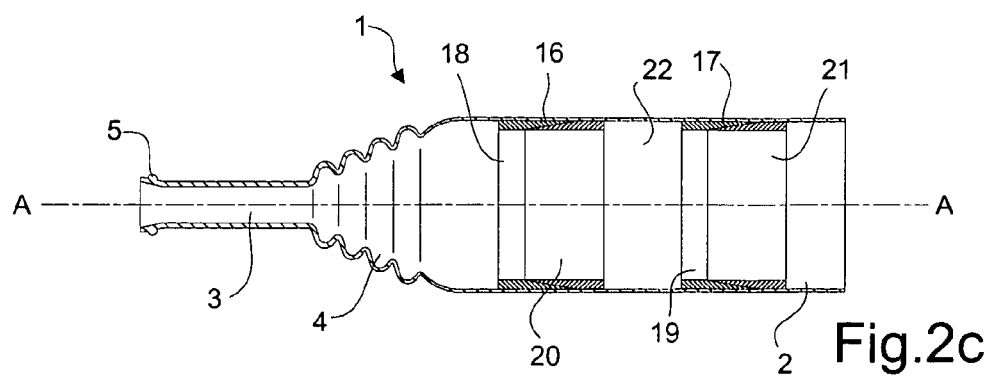

A third embodiment is shown in FIG. 2c wherein there is provided a first section 16 and a second section 17 of adhesive bands separated by an area 22 with no adhesive. Each section comprises a first adhesive 18,19 and a second adhesive 20,21. The adhesive bands within each section overlap each other. The overlap shows different adhesive characteristic and thus, by only using two adhesives an even broader user range can be provided than described above where the adhesive bands abut.

As can be seen from the described embodiments with reference to FIGS. 2a-2c an area 8;15;22 with no adhesive is provided which separates a number of adhesive bands in order to define the barriers which reduce the risk of leakage.

Although not shown in the figures the area can additionally be provided with one or more materials different from the urisheath. Such materials can for example be a skin caring material, an absorbing material or an indicating material. The indicating material being a material which changes color when in contact with a substance, for example the urea in urine. This visually indicates when a barrier has been broken and the user should change the urisheath.

Furthermore, it should be understood that it is not essentially that an area separates the adhesive bands. As described with reference to FIGS. 2b and 2c advantages such as providing improved adhesive within a larger group of users can also be realized by only providing a single section comprising of two or more abutting or overlapping adhesive bands.

REFERENCE NUMBERS 1. urisheath
2. sheath portion
3. tip portion
4. corrugated portion
5. rib
6. first adhesive band
7. second adhesive band
8. area
9. first section
10. second section
11,12. first adhesive band
13,14. second adhesive band
15. area
16. first section
17. second section
18,19. first adhesive
20,21. second adhesive

The invention claimed is:

1. An external urinary catheter comprising:
   a tip portion, a sheath portion, and a first ring of adhesive and a second ring of adhesive; said first and second rings of adhesive are disposed on an inside surface of the sheath portion;
   said first ring of adhesive being separated from the second ring of adhesive by a skin care area;
   each of said first and second rings of adhesive comprising a first continuous band of a first adhesive and a second continuous band of a second adhesive, said first continuous band touching said second continuous band, wherein each of the first and second continuous bands is disposed perpendicular to a longitudinal axis of the sheath portion;
   said first adhesive is configured for wet-tack adherence to the skin; and
   said second adhesive is different from said first adhesive and is configured for dry-tack adherence to skin.

2. The external urinary catheter of claim 1, wherein the tip portion comprises a corrugated tip portion.

3. The external urinary catheter of claim 1, further comprising:
   a rib disposed at an end of the tip portion, the rib configured to allow the tip portion to couple to a urinary catheter.

4. The external urinary catheter of claim 1, wherein the first continuous band overlaps the second continuous band.

* * * * *